United States Patent
Dean et al.

(10) Patent No.: US 6,797,255 B1
(45) Date of Patent: Sep. 28, 2004

(54) METHODS AND COMPOSITIONS FOR ENHANCING MAGNETIC RESONANCE IMAGING

(75) Inventors: Richard T. Dean, Chesterfield, MO (US); George Brooke Hoey, St. Louis, MO (US)

(73) Assignee: Mallinckrodt Inc., St. Louis, MO (US)

( * ) Notice: Subject to any disclaimer, the term of this patent is extended or adjusted under 35 U.S.C. 154(b) by 1826 days.

(21) Appl. No.: 07/777,793

(22) Filed: Oct. 17, 1991

Related U.S. Application Data

(63) Continuation of application No. 07/332,167, filed on Apr. 3, 1989, now abandoned, which is a continuation of application No. 07/075,413, filed on Jul. 20, 1987, now abandoned, which is a continuation of application No. 06/905,765, filed on Sep. 9, 1986, now abandoned, which is a continuation of application No. 06/692,514, filed on Jan. 18, 1985, now abandoned.

(51) Int. Cl.⁷ .................... A61K 49/00; A61K 31/195
(52) U.S. Cl. ........................... 424/9; 514/563
(58) Field of Search ............... 424/9; 514/563

(56) References Cited

U.S. PATENT DOCUMENTS

| | | | |
|---|---|---|---|
| 4,308,249 A | * 12/1981 | Frank et al. | 424/9 |
| 4,418,208 A | * 11/1983 | Nunn et al. | 502/449 |
| 4,472,509 A | * 9/1984 | Gansow et al. | 436/548 |
| 4,647,447 A | * 3/1987 | Gries et al. | 424/9 |

OTHER PUBLICATIONS

Rvnge et al., AJR, vol. 141, (1983), pp. 1209–1215.*

* cited by examiner

Primary Examiner—Russell Travers
(74) Attorney, Agent, or Firm—S

(57) ABSTRACT

Substantially nontoxic manganese complexes of compounds of the formula:

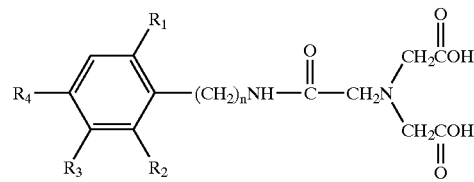

wherein n=0, 1 or 2, $R_1$ and $R_2$ are hydrogen or alkyl groups of 1 to 4 carbon atoms, and $R_3$ and $R_4$ are hydrogen, alkyl groups of 1 to 4 carbon atoms or halogen, are useful for enhancing magnetic resonance images of body organs and tissues. Illustrative manganese complexes of such compounds include dihydrogen bis(N-[N'-(2,6-Diisopropylphenyl)-carbamoylmethyl-]iminodiaceto) manganese(II) monohydrate, dihydrogen bis[N-[N'-(2,6-dimethylphenyl)-carbamoylmethyl]iminodiaceto)-manganese(II) trihydrate, and dihydrogen bis(N-[N'-(2,6-dimethylpheny)carbamoylmethyl]iminodiaceto) manganese (II) dihydrate.

13 Claims, No Drawings

METHODS AND COMPOSITIONS FOR ENHANCING MAGNETIC RESONANCE IMAGING

This is a continuation, of application Ser. No. 07/332,167 filed Apr. 3, 1989, now abandoned, which is a continuation of application Ser. No. 07/075,413 filed Jul. 20, 1987, now abandoned, which is a continuation of application Ser. No. 06/905,765 filed Sep. 9, 1986, now abandoned, which is a continuation of application Ser. No. 06/692,514 filed Jan. 18, 1985, now abandoned.

BACKGROUND OF THE INVENTION

This invention relates to magnetic resonance imaging (MRI), also referred to as nuclear magnetic resonance (NMR) imaging, and more particularly, to methods and compositions for enhancing magnetic resonance images of body organs and tissues.

The recently developed techniques of MRI or NMR imaging encompasses the detection of certain atomic nuclei utilizing magnetic-fields and radio-frequency radiation. It is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g., protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei precess at a frequency f=42.6 MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, x-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by x-ray or CT which are only sensitive to differences in the electron density of tissue. The images obtainable by MRI techniques also enable the physician to detect structures smaller than those detectable by CT and thereby provide comparable or better spatial resolution.

N-substituted iminodiacetic acids, such as methyliminodiacetic acid (MIDA) and N-(2,6-dimethylphenylcarbamoylmethyl)iminodiacetic acid (HIDA), labeled with technetium –99m, cobalt-57 and other radiometals have been used as radio-pharmaceutical imaging agents for the liver or hepatobiliary system. In this regard, reference is made to U. S. Pat. Nos. 4,308,249, 4,316,883, 4,318,898, 4,350,674 and 4,418,208 and to J. Nucl. Med. 17:633–638 (1976) and J. Nucl. Med. 17(6), 545 (1976).

SUMMARY OF THE INVENTION

Among the several objects of the invention may be noted the provision of novel compositions for enhancing magnetic resonance images of body organs and tissues; the provision of such compositions which contain a substantially non-toxic manganese complex of certain N-(dialkylphenylcarbamoylmethyl)iminodiacetic acid compounds; and the provision of methods for enhancing magnetic resonance images of body organs and tissues through the administration of such compositions. Other objects and features will be in part apparent and in part pointed out hereinafter.

Briefly, the invention is directed to compositions for enhancing magnetic resonance images of body organs and tissues, the composition comprising a substantially nontoxic manganese complex of a compound of the formula:

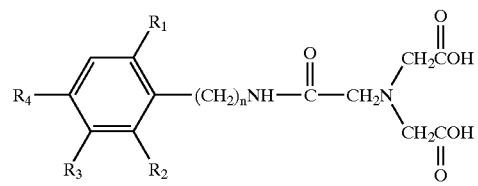

wherein n=0, 1 or 2, $R_1$ and $R_2$ are hydrogen or alkyl groups of 1 to 4 carbon atoms, and $R_3$ and $R_4$ are hydrogen, alkyl groups of 1 to 4 carbon atoms or halogen. The invention is also directed to methods for enhancing magnetic resonance images of body organs and tissues by administering such compositions to a mammal in sufficient amounts to provide enhancement of magnetic resonance images of the body organs and tissues.

DESCRIPTION OF THE PREFERRED EMBODIMENTS

In accordance with the present invention, it has now been found that magnetic resonance images of body organs and tissues may be usefully enhanced through the administration to a mammal of a substantially nontoxic manganese complex of a compound of the formula:

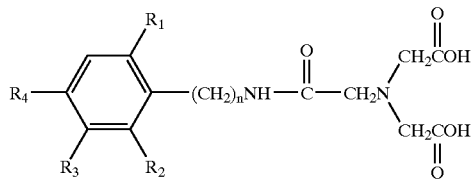

wherein n=0, 1 or 2, $R_1$ and $R_2$ are hydrogen or alkyl groups of 1 to 4 carbon atoms, and $R_3$ and $R_4$ are hydrogen, alkyl groups of 1 to 4 carbon atoms or halogen.

Manganese is a paramagnetic element capable of altering or enhancing magnetic resonance images, i.e. it is capable of altering the magnetic resonance signal characteristics of body tissues, organs or fluids and thus aid in differentiating normal from diseased tissue. Administered as a free ionic salt (e.g. chloride), it may also exhibit some target organ specificity (e.g. liver). However, such paramagnetic salts or compounds may undesirably exhibit significant toxicity.

In accordance with the present invention, we have found that manganese complexes of the above-noted compounds are relatively or substantially nontoxic and are therefore useful for enhancing magnetic resonance images by favorably altering relaxation times $T_1$ and $T_2$ and thereby affording improved contrast between normal and diseased tissues or organs. Illustrative manganese complexes of the aforementioned class of compounds which may be used in carrying out the invention include manganese complexes of N-[N'-(2,6-diisopropylphenylcarbamoylmethyl]iminodiacetic acid, N-[N'-(2,6-diethyl-4,5-dimethylphenyl)carbamoylmethyl]iminodiacetic acid, N-[N'-(2,6-dimethyl-4,5-difluorophenyl)carbamoylmethyl]iminodiacetic acid, N-[N'-(4-fluoro-2,5,6-trimethylphenyl)carbamoylmethyl]iminodiacetic acid and N-[N'-(5-bromo-2,4,6-trimethylphenyl)carbamoylmethyl]iminodiacetic acid. Compounds of the aforementioned formula wherein n is 0 are preferred. The manganese complexes of the invention may be in the form of mono-, di or trihydrates.

As shown by the toxicity studies set forth hereinafter, a representative member of the class of manganese complexes herein contemplated, namely, dihydrogen bis(N-[N'-(2,6-dimethylphenyl)carbamoylmethyl]iminodiaceto)-manganese(II) trihydrate, possesses a favorable intravenous toxicity profile and dramatically reduces hepatic and biliary $T_1$ relaxation times. In contrast, a gadolinium complex of the same class, namely, hydrogen bis(N-[N'-(2,6-dimethylphenyl)carbamoylmethyl]iminodiaceto) gadolinium(III) dihydrate, possesses a relatively poor toxicity profile (LD$_{50}$ of about 0.2 mmol/kg with persistent, delayed toxicity) and also has relatively poor $T_1$ and $T_2$ lowering effects in the liver.

The substantially nontoxic manganese complexes of the present invention are administered to a mammal in a sufficient amount to provide enhancement of magnetic resonance images of body organs and tissues prior to obtaining a magnetic resonance scan or scans of such organs and tissues with "slices" being taken at the level of the desired organ at various time periods post-administration.

The following examples illustrate the practice of the invention:

EXAMPLE 1

Preparation of Dihydrogen Bis(N-[N'-2,6-Diisopropylphenyl)carbamoylmethyl]iminodiaceto) manganese(II) Hydrate N-[N'-(2,6-Diisopropylphenyl)carbamoylmethyl] iminodiace tic acid (2 g, 0.0064 mole), NaOH (0.2 g) and deionized water (10 ml) were stirred until a turbid solution was formed. To this was added a 50% ethanol solution (20 ml), followed by manganese(II) chloride (0.38 g) which had been dissolved in ethanol (10 ml). The solution was stirred overnight and the product precipitated out. This was collected and washed with 1:1 ethanol/water (50 ml) and with anhydrous diethyl ether (100 ml). The solid was dried in an Abderholden drying pistol over $P_2O_5$ at hexane reflux temperature and under high vacuum (0.1 mm).

The results of elemental analysis were as follows: calculated for $C_{18}H_{24}N_2O_5Mn$; $H_2O$; C, 51.06; H, 6.14; N, 6.62; Mn, 12.97; $H_2O$, 4.25. Found: C, 51.73; H, 6.34; N, 6.52; Mn 12.36; $H_2O$, 4.25.

The complex, dihydrogen bis(N-[N'-(2,6-diisopropylphenyl)carbamoylmethyl]iminodiaceto) manganese(II) hydrate, was thus isolated as the hydrated species. The solubility of the complex in water was determined to be approximately 0.1% w/v. The relaxation parameters $T_1$ and $T_2$ of a $10^{-3}$M solution of the complex in a 90 MHz NMR experiment were determined to be 0.107 sec. and 0.007 sec. respectively. The $T_1$ and $T_2$ values for water are 2.51 sec. and 0.150 sec., respectively.

EXAMPLE 2

Preparation of Dihydrogen Bis(N-[N'-2,6-dimethylphenyl)carbamoylmethyl]iminodiaceto) manganese(II) Trihydrate N-[N'-(2,6-Dimethylphenyl)carbamoylmethyl] iminodiaceti acid (10 g) was dissolved in, a sodium hydroxide solution (1.36 g NaOH in 50 ml $H_2O$). The solution was filtered and to this was added manganese(II) chloride (4.38 g) which had been dissolved in ethanol (50 ml). A pinkish precipitate formed after stirring for one minute. The reaction mixture was stirred for 2 hours, the solid collected via filtration, washed with a 50% ethanol in water solution and dried 18 hours in a forced air oven at 60° C.

The results of elemental analysis were as follows:

calculated for [Mn ($C_{28}H_{34}N_4O_{10}$)]. 3$H_2O$: C, 48.49; H, 5.52; N, 8.08; Mn, 7.92. Found: C, 48.98; H, 5.75; N, 7.95: Mn, 8.03.

The solubility of the complex in water was determined to be 2.5% w/v, approximately 3.6×10$^{-3}$M. The relaxation parameters $T_1$ and T2 of a $10^{-3}$M solution of the complex in a 90 MHz NMR experiment were determined to be 126 milliseconds and 1.5 milliseconds, respectively.

EXAMPLE 3

Preparation of Dihydrogen Bis(N-[N'-(2,6-dimethylphenyl)carbamoylmethyl]iminodiaceto) manganese(II) Dihydrate Dihydrogen bis(N-N'-(2,6-dimethylphenyl) carbamoylmethyl]iminodiaceto)manganese(II) dihydrate was prepared by the procedure set forth in Example 2 except that the mole ratio of water to the complex was 2.11.

The results of elemental analysis were as follows: Calculated for [Mn($C_{28}H_{34}N_4O_{10}$)]. 2$H_2O$: C, 49.63; H, 5.65; N, 8.27; Mn, 8.11. Found: C, 49.27, H, 5.8; N, 8.18; Mn, 8.11.

EXAMPLE 4

Acute Intravenous Toxicity Determination of Dihydrogen Bis(N-[N'-(2,6-dimethylphenyl)carbamoylmethyl]iminodiaceto)manganese(II) Trihydrate Dihydrogen Bis(N-[N'-(2,6-dimethylphenyl)carbamoylmethyl]iminidiaceto)manganese(II) trihydrate was dissolved in 0.9% sodium chloride Inj. USP as a 1.25% solution.

Male and female Swiss CF-1 mice with a body weight range of 17.4 to 24.2 grams were used. The mice were housed according to standard procedures and individually marked with picric acid.

The dose schedule was as follows:

| DOSE (mmol/kg) | DOSE (ml/kg) | NUMBER OF MICE MALE | NUMBER OF MICE FEMALE |
|---|---|---|---|
| 0.360 | 20 | 2 | 2 |
| 0.540 | 30 | 2 | 2 |
| 0.630 | 35 | 2 | 2 |

Measured single doses were injected into the lateral tail vein at a rate of 1 ml/min. The animals were observed immediately after dosing and during the 7-day observation period for pharmacotoxic reactions. Recording of terminal body weights and general necropsy of the thoracic and abdominal organs was performed after 7 days.

Mortality data are presented below:

| DOSE (mmol/kg) | IMMEDIATE | 1 | 2 | 3 | 4 | 5 | 6 | 7 | BODY WEIGHT CHANGE (g) |
|---|---|---|---|---|---|---|---|---|---|
| 0.360 | 0/4 | 0/4 | 0/4 | 0/4 | 0/4 | 0/4 | 0/4 | 0/4 | +1.75 |
| 0.540 | 2/4 | 2/4 | 2/4 | 2/4 | 2/4 | 2/4 | 2/4 | 2/4 | +2.0 |
| 0.630 | 3/4 | 3/4 | 3/4 | 3/4 | 3/4 | 3/4 | 3/4 | 3/4 | +1.6 |

(Columns 1–7 are MORTALITIES/NUMBER TESTED, DELAYED (DAYS AFTER DOSING))

The $LD_{50}$ for dihydrogen bis(N-[N'-(2,6-dimethylphenyl)carbamoylmethyl]iminodiaceto)-manganese(II) trihydrate is approximately 0.540 mmol/kg. Mild to severe convulsions occurred in all the animals immediately after injections. All mortalities occurred shortly after dosing. The surviving animals displayed mild to severe depression which was resolved within one hour after dosing Necrospies did not reveal any abnormalities. Weight gains were normal.

EXAMPLE 5

Effect of Dihydrogen Bis(N-[N'-(2,6-dimethylphenyl)carbamoylmethyl]iminodiaceto)manganese(II) Trihydrate on Tissue Proton $T_1$ and $T_2$ Relaxation Times All experiments employing the complex dihydrogen bis(N-[N'-(2,6-dimethylphenyl)carbamoylmethyl]iminodiaceto)manganese (II) trihydrate were conducted following intravenous administration to rabbits. A 10 mM solution of the complex was used in these studies. Rabbits were anesthetized with ketamine/xylazine prior to treatment. The results given were obtained with a 10 mHz RADX proton spin analyzer.

Dose-response experiments were conducted on rabbits following intravenous injection of 0.01–0.10 mmol of the complex/kg. Animals were killed 15 min after injection and tissue $T_1$ and $T_2$ relaxation times were determined. The data obtained are summarized in Tables 1 and 2.

TABLE 1

Mean Tissue Proton $T_1$ and $T_2$ Relaxation Times 15 Minutes After Intravenous Administration[a]

| | Control[b] | | 0.01 | | 0.03 | | 0.08 | | 0.10 | |
|---|---|---|---|---|---|---|---|---|---|---|
| Tissue | $T_1$ | $T_2$ | $T_1$ | $T_2$ | $T_1$ | $T_2$ | $T_1$ | $T_2$ | $T_1$ | $T_2$ |
| Blood, Pretreatment | — | — | 652 | 170 | 615 | 155 | 586 | 153 | 616 | 158 |
| Blood, 5 min | — | — | 554 | 161 | 192 | 110 | 70 | 56 | 64 | 55 |
| Blood, 10 min | — | — | 604 | 165 | 283 | 119 | 96 | 72 | 398 | 179 |
| Blood, 15 min | — | — | 639 | 171 | 368 | 141 | 115 | 82 | — | — |
| Heart | 410 | 57 | 370 | 64 | 222 | 56 | 104 | 43 | 84 | 39 |
| Lung | 484 | 91 | 464 | 91 | 352 | 100 | 222 | 67 | 144 | 62 |
| Fat | 139 | 125 | 148 | 129 | 136 | 122 | 125 | 122 | 122 | 89 |
| Skeletal Muscle | 352 | 38 | 364 | 35 | 304 | 38 | 255 | 39 | 205 | 38 |
| Renal Cortex | 275 | 69 | 236 | 77 | 164 | 63 | 77 | 42 | 71 | 37 |

TABLE 1-continued

Mean Tissue Proton $T_1$ and $T_2$ Relaxation Times 15 Minutes After Intravenous Administration[a]

| | | | Dose Level - mmol/kg | | | | | | | |
|---|---|---|---|---|---|---|---|---|---|---|
| | Control[b] | | 0.01 | | 0.03 | | 0.08 | | 0.10 | |
| Tissue | $T_1$ | $T_2$ | $T_1$ | $T_2$ | $T_1$ | $T_2$ | $T_1$ | $T_2$ | $T_1$ | $T_2$ |
| Renal Medulla | 546 | 121 | 435 | 122 | 218 | 95 | 124 | 74 | 35 | 21 |
| Liver | 205 | 52 | 92 | 41 | 49 | 25 | 28 | 18 | 143 | 87 |
| Spleen | 377 | 74 | 346 | 73 | 260 | 70 | 195 | 65 | 202 | 71 |
| Pancreas | 205 | 70 | 225 | 66 | 104 | 118 | 101 | 70 | 149 | 69 |
| Bladder | 439 | 72 | 380 | 84 | 312 | 68 | 173 | 60 | 159 | 61 |
| Stomach | 284 | 56 | 287 | 56 | 199 | 53 | 122 | 43 | 121 | 47 |
| Small Intestine | 286 | 64 | 219 | 73 | 150 | 60 | 130 | 50 | 141 | 45 |
| Large Intestine | 284 | 63 | 245 | 65 | 155 | 52 | 123 | 43 | 166 | 53 |

[a]$T_1$ and $T_2$ relaxation times were determined using a 10 mHz RADX proton spin analyzer and are expressed in msec. For the treatment groups, N=4 rabbits/dose level with the exception of the 0.10 mmol/kg group which represents 1 rabbit. Blood values for the 0.08 mmol/kg group are derived from 3 rabbits.
[b]Control values represent the mean values determined for untreated rabbits in a 10 mHz RADX proton spin analyzer, N=18 rabbits.

TABLE 2

Approximate Effective Intravenous Dose Required to Reduce Tissue $T_1$ and $T_2$ Relaxation Times by 50% $(ED_{50})$[a]

| | APPROXIMATE $ED_{50}$ (mmol/kg) | |
|---|---|---|
| TISSUE | $T_1$ | $T_2$ |
| Heart | 0.037 | 0.38 |
| Lung | 0.075 | 0.15 |
| Fat | 11.94 | — |
| Skeletal muscle | 0.35 | — |
| Renal cortex | 0.041 | 0.14 |
| Renal medulla | 0.030 | 0.90 |
| Liver | 0.0067 | 0.04 |
| Spleen | 0.085 | — |
| Pancreas | 0.064 | — |
| Bladder | 0.060 | 0.51 |
| Stomach | 0.068 | 0.93 |
| Small Intestine | 0.051 | 0.27 |
| Large Intestine | 0.050 | 0.19 |

[a]$T_2ED_{50}$ values for fat, skeletal muscle, spleen and pancreas could not be determined from the dose levels employed.

A dose-related decrease in tissue $T_1$ relaxation times was observed following injection of the complex. The liver, kidneys and heart exhibited the greatest relative change in $T_1$ values, whereas fat exhibited a minimal decrease in $T_1$ relaxation time at the dose levels of the complex employed in the study. Estimated ED50 values, the effective intravenous dose of the complex required to cause a 50% reduction in tissue $T_1$ relaxation time are summarized in Table 2. Tissue $T_2$ relaxation times were, in general, minimally affected by intravenous injection of the complex with the liver $T_2$ times exhibiting the greatest sensitivity to the complex.

A second study was performed in two rabbits killed 45 min after intravenous injection of 0.03 mmol of the complex/Kg to examine the time course of $T_1$ and $T_2$ relaxation enhancement. The results are summarized in Table 3.

TABLE 3

Mean Tissue $T_1$ and $T_2$ Relaxation Times at 15 and 45 Minutes After Intravenous Injection of 0.03 mmol/kg[a]

| | $T_1$ | | $T_2$ | |
|---|---|---|---|---|
| Tissue | 15 min | 45 min | 15 min | 45 min |
| Heart | 222 | 265 | 56 | 57 |
| Lung | 352 | 438 | 100 | 89 |
| Fat | 136 | 137 | 122 | 125 |
| Skeletal muscle | 304 | 315 | 38 | 41 |
| Renal cortex | 164 | 143 | 63 | 57 |
| Renal medulla | 218 | 244 | 95 | 91 |
| Liver | 49 | 37 | 25 | 24 |
| Spleen | 260 | 271 | 70 | 71 |
| Pancreas | 104 | 117 | 118 | 75 |
| Bladder | 312 | 367 | 68 | 72 |
| Stomach | 199 | 159 | 53 | 47 |
| Small Intestine | 150 | 129 | 60 | 48 |
| Large Intestine | 155 | 154 | 52 | 47 |

[a]$T_1$ and $T_2$ relaxation times were determined using a 10 mHz RADX proton spin analyzer and are expressed in msec.
Values represent the mean of 4 rabbits at 15 min and 2 rabbits at 45 min.

In general, tissue $T_1$ relaxation times were decreased to the same extent as noted at 15 min after injection of 0.03 mmol of the complex/kg. $T_2$ values were similar to the values obtained at 15 min after injection of the complex.

In a third study, one rabbit received 0.03 mmol of the complex/kg and bile samples were collected at 5–20 min intervals over a 105 min time course and proton $T_1$ and $T_2$ relaxation times were determined. Control bile $T_1$ relaxation time was 944 msec. within 1 min of injection, bile $T_1$ was reduced to 60 msec. Over the 105 minute time course, bile $T_1$ returned to a value of 91 msec, less than 10% of the preinjection control value. The preinjection bile $T_2$ relaxation time was 16 msec. Following injection of the complex, bile $T_2$ relaxation times gradually increased to 44 msec.)

In another study, employing an intravenous dose of 0.05 mmol of the complex/Kg, one rabbit was killed at time points of 5 min, 15 min or 1 week after dosing. In animals killed at 5 and 15 min, heart and liver $T_1$ and $T_2$ relaxation times were determined with 5 and 10 mHz instruments. The results indicate that the complex reduced tissue $T_1$ values at both frequencies. In the rabbit killed at 1 week, tissue $T_1$ and $T_2$ relaxation times had returned to control values.

Thus, intravenous administration of the complex dihydrogen bis(N-[N'-(2,6-dimethylphenyl)carbamoylmethyl]-iminodiaceto)manganese(II) trihydrate dramatically reduced hepatic and biliary $T_1$ relaxation times. The $ED_{50}$ for hepatic $T_1$ enhancement was less than 0.01 mmol/kg. Based upon the estimated acute mouse intravenous $LD_{50}$ value of 0.5 mmol/kg, the diagnostic safety ratio for the complex as a heptobiliary MRI proton relaxation enhancement agent is approximately 50.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A composition for enhancing magnetic resonance images of body organs and tissues, the composition comprising a substantially nontoxic manganese complex of a compound of the formula:

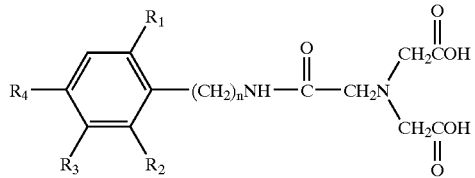

wherein n=0, 1 or 2, $R_1$ and $R_2$ are hydrogen or alkyl groups of 1 to 4 carbon atoms, and $R_3$ and $R_4$ are hydrogen, alkyl groups of 1 to 4 carbon atoms or halogen.

2. A composition of claim 1 wherein said compound is N-[N'-(2,6-diisopropylphenyl)carbamoylmethyl]iminodiacetic acid.

3. A composition of claim 1 wherein said compound is N-(N'-(2,6-dimethylphenyl)carbamoylmethyl)iminodiacetic acid.

4. Dihydrogen bis(N-[N'-(2,6-diisopropylphenyl)carbamoylmethyl]iminodiaceto)manganese(II) monohydrate.

5. Dihydrogen bis(N-[N'-(2,6-dimethylphenyl)carbamoyl-methyl]iminodiaceto)manganese(II) trihydrate.

6. Dihydrogen bis(N-[N'-(2,6-dimethylphenyl)carbamoylmethyl]iminodiaceto)manganese(II) dihydrate.

7. A method for enhancing magnetic resonance images of body organs and tissues which comprises administering to a mammal a composition comprising a substantially nontoxic manganese complex of a compound of the formula:

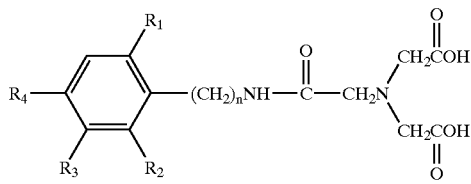

wherein n=0, 1 or 2, $R_1$ and $R_2$ are hydrogen or alkyl groups of 1 to 4 carbon atoms, and $R_3$ and $R_4$ are hydrogen, alkyl groups of 1 to 4 carbon atoms or halogen, in a sufficient amount to provide enhancement of magnetic resonance images of said body organs and tissues.

8. A method for enhancing magnetic resonance images of body organs and tissues as set forth in claim 7 wherein said compound is N-[N'-(2,6-diisopropylphenyl)carbamoylmethyl]iminodiacetic acid.

9. A method for enhancing magnetic resonance images of body organs and tissues as set forth in claim 7 wherein said compound is N-[N'-(2,6-dimethylphenyl)carbamoylmethyl]iminodiacetic acid.

10. A method for enhancing magnetic resonance images of body organs and tissues as set forth in claim 7 wherein said composition is dihydrogen bis(N-[N'-(2,6-diisopropylphenyl)carbamoylmethyl]iminodiaeto)manganese(II) monohydrate.

11. A method for enhancing magnetic resonance images of body organs and tissues as set forth in claim 7 wherein said composition is dihydrogen bis(N-[N'-(2,6-dimethylphenyl)carbamoylmethyl]iminodiaceto)manganese(II) trihydrate.

12. A method for enhancing magnetic resonance images of body organs and tissues as set forth in claim 7 wherein said composition is dihydrogen bis(N-[N'-(2,6-dimethylphenyl)carbamoylmethyl]iminodiaceto)manganese(II) dihydrate.

13. A method for enhancing magnetic resonance images of body organs and tissues as set forth in claim 7 wherein magnetic resonance images of the hepatobiliary system are enhanced.

* * * * *

UNITED STATES PATENT AND TRADEMARK OFFICE
CERTIFICATE OF CORRECTION

PATENT NO. : 6,797,255 B1  
DATED : September 28, 2004  
INVENTOR(S) : Richard T. Dean It is certified that error appears in the above-identified patent and that said Letters Patent is hereby corrected as shown below:

Title page,
Item [*] Notice, "by 1,826 days" should read -- by 0 days --.

Signed and Sealed this

Eleventh Day of January, 2005

JON W. DUDAS  
*Director of the United States Patent and Trademark Office*